United States Patent [19]

Woodard et al.

[11] Patent Number: 5,625,054

[45] Date of Patent: Apr. 29, 1997

[54] DNA PURIFICATION BY SOLID PHASE EXTRACTION USING FLUORINATED CELITE

[75] Inventors: Daniel L. Woodard; Adriann J. Howard, both of Raleigh; James A. Down, Cary, all of N.C.

[73] Assignee: Becton Dickinson and Company, Franklin Lakes, N.J.

[21] Appl. No.: 450,036

[22] Filed: May 25, 1995

Related U.S. Application Data

[62] Division of Ser. No. 127,407, Sep. 27, 1993, Pat. No. 5,438,129.

[51] Int. Cl.$^6$ .................................................. C07H 21/04
[52] U.S. Cl. ............... 536/25.4; 536/25.41; 536/25.42; 423/2; 423/118.1; 423/325; 423/341; 423/495; 423/620; 252/302; 252/315.5; 252/315.6; 252/315.7; 502/407; 502/408; 502/412; 502/414
[58] Field of Search .................. 536/25.4, 25.41, 536/25.42; 423/2, 118, 325, 341, 343, 495, 629; 252/302, 315.5, 315.6, 315.7; 502/412, 414, 407, 408

[56] References Cited

U.S. PATENT DOCUMENTS

| | | | |
|---|---|---|---|
| 2,982,053 | 5/1961 | Elmer | 501/54 |
| 3,314,772 | 4/1967 | Poole et al. | 65/30.13 |
| 3,508,895 | 4/1970 | Poole et al. | 65/30.14 |
| 3,511,605 | 5/1970 | Smith et al. | 423/335 |
| 4,169,790 | 10/1979 | Pretorius et al. | 210/31 |
| 4,363,792 | 12/1982 | Gibbs et al. | 423/335 |
| 4,504,595 | 3/1985 | Jacques et al. | 502/224 |

(List continued on next page.)

FOREIGN PATENT DOCUMENTS

| | | |
|---|---|---|
| 0130055 | 1/1985 | European Pat. Off. . |
| 0295418 | 12/1988 | European Pat. Off. . |
| 0512768 | 11/1992 | European Pat. Off. . |
| 0555798 | 8/1993 | European Pat. Off. . |
| 1286769 | 1/1962 | France . |
| 3545610 | 6/1987 | Germany . |
| 1051314 | 2/1989 | Japan . |
| 1176447 | 7/1989 | Japan . |
| 1188538 | 7/1989 | Japan . |
| 0763264 | 9/1980 | U.S.S.R. . |
| 0835959 | 6/1981 | U.S.S.R. . |
| 2108949 | 5/1983 | United Kingdom . |

OTHER PUBLICATIONS

Marko et al., "A Procedure for the Large–Scale Isolation of Highly Purified Plasmid DNA Using Alkaline Extraction and Binding to Glass Powder," *Anal. Biochem.*, 121, 382–387(1982).

Vogelstein et al., "Preparative and Analytical Purification of DNA from Agarose," *Proc. Nat. Acad. Sci. USA*, 76(2), 615–619 (1979).

(List continued on next page.)

*Primary Examiner*—John Kight
*Assistant Examiner*—L. Eric Crane
*Attorney, Agent, or Firm*—David W. Highet, Esq.

[57] ABSTRACT

The present invention relates to fluorinated surfaces which exhibit sufficient hydrophilicity and sufficient electropositivity to bind DNA from a suspension containing DNA and permit elution of the DNA from the surface. Generally, the hydrophilic and electropositive characteristics are expressed at the fluorinated surface. Preferred fluorinated surfaces of the present invention include fluorinated Al(OH)$_3$, fluorinated SiO$_2$ and fluorinated Celite. The fluorinated surfaces of the present invention are particularly useful in processes for purification of DNA from other cellular components. In these processes, a suspension of cellular components is placed in contact with the fluorinated surface, the fluorinated surface is washed to remove all cellular components other than DNA which are bound to the surface, and the bound DNA is eluted from the surface. Lower concentrations of chaotrope in the binding buffer are needed to bind DNA to the fluorinated surfaces.

2 Claims, No Drawings

U.S. PATENT DOCUMENTS

| | | | |
|---|---|---|---|
| 4,629,485 | 12/1986 | Berkey | 65/3.11 |
| 4,746,572 | 5/1988 | Glajch et al. | 428/403 |
| 4,836,954 | 6/1989 | Rittler | 252/378 R |
| 4,837,195 | 6/1989 | Cox et al. | 502/408 |
| 4,935,342 | 6/1990 | Seligson et al. | 435/6 |
| 5,022,990 | 6/1991 | Doi et al. | 210/500.42 |
| 5,032,266 | 7/1991 | Kirkland et al. | 210/198.2 |
| 5,075,430 | 12/1991 | Little | 536/25.42 |
| 5,155,018 | 10/1992 | Gillespie et al. | 435/91 |
| 5,207,915 | 5/1993 | Hagen et al. | 210/635 |
| 5,234,809 | 8/1993 | Boom et al. | 435/91 |
| 5,438,129 | 8/1995 | Woodard et al. | 536/25.4 |

OTHER PUBLICATIONS

Boom et al.(II), "Rapid and Simple Method for Purification of Nucleic Acids," *J. Clin. Microbiol.*, 28(3), 495–503 (1990).

Willis et al., "Prep–A–Gene™: A Superior Matrix for the Purification of DNA and DNA Fragments," *Biotechniques*, 9(1), 92–99 (1990).

Lutze et al., "A Quick and Efficient Method for the Recovery of Plasmid or Viral DNA from Mammalian Cells," *Nucleic Acids Res.*, 18(20), 6150 (1990).

Chow et al., "Quantitation of DNA Fragmentation Using Fiberglass Filters," *Anal. Biochem.*, 183, 42–45 (1989).

McCormick, "A Solid–Phase Extraction Procedure for DNA Purificiation," *Anal. Biochem.*, 181, 66–74 (1989).

Upadhyay et al., "Adsorption of Nucleic Acids at the Alumina–Water Interface," *Biochem. Biophys. Acta*, 161, 561–563 (1968).

DNA PURIFICATION BY SOLID PHASE EXTRACTION USING FLUORINATED CELITE

This is a division of application Ser. No. 08/127,407, filed Sep. 27, 1993, now U.S. Pat. No. 5,438,129.

BACKGROUND OF THE INVENTION

The present invention relates generally to the purification of DNA by solid phase extraction, and more specifically to fluorinated surfaces which are capable of binding DNA and eluting DNA under suitable conditions.

The preparation of high-purity double-stranded (ds) plasmid DNA, single-stranded (ss) phage DNA, chromosomal DNA and agarose gel-purified DNA fragments is of critical importance in molecular biology. Ideally, a method for purifying DNA should be simple, rapid and require little, if any, additional sample manipulation. DNA rendered by such a method should be immediately amenable to transformation, restriction analysis, ligation or sequencing. A method with all of these features would be extremely attractive in the automation of DNA sample preparation, a goal of research and diagnostic laboratories. Typically, the preparation of plasmid DNA from crude alcohol precipitates is laborious, most often utilizing CsCl gradients, gel filtration, ion exchange chromatography, or RNase, proteinase K and repeated alcohol precipitation steps. These methods also require considerable downstream sample preparation to remove CsCl and other salts, ethidium bromide and alcohol. Similar arguments extend when using any of these methods for purifying DNA fragments. A further problem with these methods is that small, negatively-charged cellular components can co-purify with the DNA. Thus, the DNA can have an undesirable level of contamination.

DNA can also be purified using solid phases. Conventional solid phase extraction techniques have utilized surfaces which either (1) fail to attract and hold sufficient quantities of DNA molecules because of surface design to permit easy recovery of the DNA molecules during elution, or (2) excessively adhere DNA molecules to the surface, thereby hindering recovery of the DNA molecules during elution. Conventional metal surfaces which cause these problems when utilized in solid phase extraction include silica surfaces such as glass and Celite. Adequate binding of DNA to these types of surfaces can be achieved only by utilizing high concentrations of chaotropes or alcohols which are generally toxic, caustic, and/or expensive. For example, it is known that DNA will bind to crushed glass powders and to glass fiber filters in the presence of chaotropes. The chaotropic ions typically are washed away with alcohol, and the DNAs are eluted with low-salt solutions or water. Importantly, RNA and protein do not bind. However, a serious drawback in the use of crushed glass powder is that its binding capacity is low. In addition, glass powders often suffer from inconsistent recovery, incompatibility with borate buffers and a tendency to nick large DNAs. Similarly, glass fiber filters provide a nonporous surface with low DNA binding capacity. Other silicas, such as silica gel and glass beads, are not suitable for DNA binding and recovery. Currently, the solid phase of choice for solid phase extraction of DNA is Celite such as found in Prep-A-Gene™ by Bio-Rad Laboratories. As with the crushed glass powders, high concentrations of chaotropes are required for adequate binding of the DNA to the Celite.

SUMMARY OF THE INVENTION

These problems with conventional DNA purification methods are addressed by the present invention, which relates to fluorinated surfaces which exhibit sufficient hydrophilicity and sufficient electropositivity to bind DNA from a suspension containing DNA and permit elution of the DNA from the surface. Generally, the hydrophilic and electropositive characteristics are expressed at the fluorinated surface, and are quantified as the presence of oxygen as measured by Fourier transform infrared spectroscopy (FTIR) and the presence of the substituted atom as detected by electron surface composition analysis (ESCA). Preferred fluorinated surfaces of the present invention include fluorinated $Al(OH)_3$, fluorinated $SiO_2$ and fluorinated Celite.

The fluorinated surfaces of the present invention are particularly useful in processes for purification of DNA from other cellular components. In these processes, a suspension of cellular components is placed in contact with the fluorinated surface, the fluorinated surface is washed to remove all cellular components other than DNA which are bound to the surface, and the bound DNA is eluted from the surface. Lower concentrations of chaotrope in the DNA binding buffer are needed to bind DNA to the fluorinated surfaces.

DETAILED DESCRIPTION OF THE INVENTION

The present invention relates to fluorinated surfaces which exhibit sufficient hydrophilicity and sufficient electropositivity to bind DNA from a suspension of cellular components and permit elution of the DNA from the surface. It has been found that much lower concentrations of chaotropes or alcohols can be utilized to achieve purification of DNA using the instant fluorinated surfaces.

DNA interacts with a solid phase surface in two ways. First, DNA interacts with the surface through hydrogen bonding between phosphate groups of DNA and surface components of the solid phase, such as surface hydroxyls. The second interaction is between the negatively charged phosphates of the DNA and positively charged elements of the solid phase surface. The hydrophilic and electropositive characteristics of the solid phase surface must be such as to allow binding of the DNA from a suspension of cellular components, a suspension of nucleic acids and other materials, and/or a suspension of nucleic acids, and to permit elution of the DNA from the solid phase surface. Thus, the electro-positive characteristics of the solid phase surface cannot have too high of a positive charge, or the DNA will stick to the surface and cannot be eluted. This characteristic is also true for many metal-based surfaces, which has resulted in their inability to be utilized for purification of DNA.

Silicon-containing materials, e.g., silica, Celite, glass powders and the like, have been used for DNA purification with mixed results. Some of these surfaces have low binding capacities and/or require the use of highly concentrated solutions of chaotropes or alcohols for the binding of DNA. Other surfaces, such as Al(OH)s, have been found to bind almost one hundred percent of DNA in a suspension, but not to elute the bound DNA. Thus, it is desired to produce solid phase surfaces, particularly solid phases of fluorinated surfaces, which exhibit suitable hydrophilic and electropositive characteristics for DNA purification and/or for DNA purification with much lower concentrations of chaotropes or alcohols. On the surface of the solid phase, hydrophilic characteristics are achieved by the presence of groups that will attract water molecules. Suitable groups include —OH, —NH, —F, —H or groups with double-bonded oxygen such as carbonyl, sulfonyl or phosphonyl. Electropositive characteristics are achieved by the presence of positively charged atoms. Suitable positively-charged atoms include Si, B or Al. In accordance with the present invention, fluorinated surfaces are prepared in which the hydrophilic characteristics are achieved by incorporation of fluorine groups, and the electropositive characteristics are achieved by incorporation of Si, Al or other appropriate positively-charged atoms. Preferred fluorinated surfaces of the present invention include fluorinated Al(OH)$_3$, fluorinated SiO$_2$ and fluorinated Celite.

In general, the fluorinated surfaces of the present invention are prepared by reacting a suitable fluoride with the desired surface. Any fluoride, preferably sodium fluoride and tetrabutylammonium fluoride, may be utilized in this reaction. It is preferred to use tetrabutylammonium fluoride. Suitable surfaces include those which bind DNA but fail to elute it. Such surfaces include Al(OH)$_3$, SiO$_2$, Celite, or any other solid that contains electropositive elements which are subject to nucleophilic attack by fluoride. Surfaces with different amounts of fluoride on the surface are prepared by reacting different proportions of fluoride and the surface. In general, the fluoride is added to the solid surface. A suitable solvent such as tetrahydrofuran (THF) is added and the reaction mixture is preferably refluxed overnight, although the reaction can be refluxed longer than 24 hours. More THF is added and the mixture heated at the above temperature overnight to keep wet. Alternatively, the reaction mixture could simply be heated overnight. The fluorinated surface is filtered, washed, air-dried briefly and oven-dried at 100° C. for ~1 hour. The fluorinated surface is then stored in a desiccator.

Fluorinated Al(OH)$_3$ surfaces are prepared as generally described above, preferably by refluxing. DNA normally binds tightly to the untreated Al(OH)$_3$ surface and is retained during elution. The presence of fluorine causes less tight bonding of DNA to the treated Al(OH)$_3$ surface due to repulsion of F($\delta$-) and the phosphate back bone of DNA, so that the bound DNA would elute from the fluorinated Al(OH)$_3$ surface during the elution step. In general, as the percentage of fluorine on the Ai(OH)s increases, the elution of DNA from the treated surface also increases. Fluorinated Al(OH)$_3$ surfaces prepared by reacting about 0.05 to about 1.5 equivalent of fluorine to Al(OH)$_3$ were found to provide good recovery of DNA from biological samples. It is preferred that the fluorinated Al(OH)$_3$ surfaces be prepared by reacting about 0.3 to about 0.9 equivalent of fluorine to Al(OH)$_3$, and most preferred that they be prepared by reacting about 0.3 equivalent of fluorine to Al(OH)$_3$. For DNA recovery, Al(OH)$_3$ fluorinated with 0.3 equivalent of fluoride out-performs super fine super floss Celite.

Fluorinated rehydrated Celite surfaces are prepared as generally described above, preferably by refluxing. DNA normally binds tightly to the untreated rehydrated Celite surface and is retained during elution. The presence of fluorine causes less tight bonding of DNA to the treated rehydrated Celite surface, so that the bound DNA would elute from the fluorinated rehydrated Celite surface during the elution step. In general, as the percentage of fluorine on the rehydrated Celite increases, the elution of DNA from the treated surface also increases. Fluorinated rehydrated Celite surfaces prepared by reacting about 0.05 equivalent to an excess of fluorine to rehydrated Celite were found to provide good recovery of DNA from biological samples. It is preferred that the fluorinated rehydrated Celite surfaces be prepared by reacting about 0.3 to about 0.9 equivalent of fluorine to rehydrated Celite. For DNA recovery, several of these fluorinated rehydrated Celite surfaces outperform super fine super floss Celite.

The fluorinated surfaces of the present invention can be used for the purification of DNA from other cellular components or potential contaminants. The DNA can be obtained from any source, including but not limited to crude cell extracts, biological fluids, phage supernatants, agarose gels and radiolabelling reactions. The DNA can be double-stranded, single-stranded, circular or linear, and can be variable in size. Conventional techniques for obtaining DNA from any source, well known in the art, are utilized to prepare the DNA for purification. Typical procedures for obtaining DNA end with a suspension of the DNA in solution. For isolation of DNA from biological samples, see, e.g., Harding, J. D. et al., *Nucleic Acids Research* 17:6947 (1989) and Marko, M. A. et al., *Analytical Biochemistry* 121:382 (1982). Procedures for isolation of plasmid DNA can be found in Lutze, L. H. et al., *Nucleic Acids Research* 20: 6150 (1990). Extraction of double-stranded DNA from biological samples can be found in Yamada, O. et al., *Journal of Virological Methods* 27:203 (1990). Most DNA solutions comprise the DNA in a suitable buffer such as TE (Tris-EDTA), TEA (40 mm Tris-acetate, 1 mm EDTA) buffer, or a lysate. See also Sambrook, J. et al., *Molecular Cloning: A Laboratory Manual*, 2nd Ed., Cold Spring Harbor Laboratory Press, New York (1989).

Once the DNA is obtained in a suitable solution or suspension, the fluorinated surface of the present invention is added to the solution or suspension. Alternatively, the DNA solution or suspension could be added to the fluorinated surface of the present invention. After the DNA solution or suspension is contacted with the fluorinated surface of the present invention, a binding buffer typically is added to assist in the binding of the DNA to the fluorinated surface. Suitable binding buffers include well-known chaotropes such as NaClO$_4$ and NaI, and other agents such as guanidine HCl or isopropanol. After the DNA is bound to the fluorinated surface, the pure DNA is eluted from the fluorinated surface. Suitable eluting agents include water or 10 mM Tris, pH 7.0. Generally, the fluorinated surface with bound DNA is separated, e.g., by centrifugation or filtration, and washed prior to eluting the DNA. Suitable washing agents include 80/20 ethanol/50 mM Tris, pH 7.0 and other low molecular weight alcohols.

The DNA obtained by purification with the fluorinated surfaces of-the present invention may be used without further manipulation for restriction enzyme digestion, cloning, sequencing, diagnostics and the like. The high quality of DNA prepared with the present invention and the speed with which DNA is purified with minimal downstream processing mean that these fluorinated surfaces can be useful in the automation of DNA sample preparation.

The present invention is described by reference to the following Examples, which are offered by way of illustration and are not intended to limit the invention in any manner. Standard techniques well known in the art or the techniques specifically described below were utilized.

EXAMPLE 1

Synthesis of Fluorinated Surfaces

A. Fluorinated Al(OH)$_3$

Fluorinated Al(OH)$_3$ surfaces comprising Al(OH)$_3$ reacted with 0.05 to 0.3 equivalent of fluoride were prepared using the following ratios of tetrabutylammonium fluoride (TBAF; Aldrich Chemical Co. ) and Al(OH)$_3$ (Aldrich):

|  | TBAF | | | Al(OH)₃ | |
|---|---|---|---|---|---|
| Rxn | eq. | ml | mMol | g | mMol |
| 1 | 0.3 | 2.20 | 2.20 | .5 | 6.67 |
| 2 | 0.1 | .700 | .700 | .5 | 6.41 |
| 3 | 0.05 | .035 | .035 | .5 | 6.41 |

Reaction 1 was performed by adding the TBAF to the solid Al(OH)₃. Ten ml THF was then added, and the mixture again was heated with stirring to reflux. Twenty ml THF was added, and the mixture was refluxed with stirring overnight. The reaction mixture was then cooled to room temperature and filtered. The fluorinated Al(OH)₃ was washed three times with 20 ml water to remove F⁻, and three times with 15 ml acetone. The washed material was air-dried for 30 minutes and heat-dried at 100° C. for 30 minutes. The dried, fluorinated Al(OH)₃ was stored in a desiccator.

Reactions 2 and 3 were performed by adding together the TBAF, Al(OH)₃ and 10–15 ml THF. A reflux condensor was attached and the reaction mixture was refluxed overnight with stirring. The reaction mixture was then cooled to room temperature and filtered. The fluorinated Al(OH)₃ was washed three times with 10 ml acetone, three times with 15 ml water and three times with 15 ml acetone. The washed material was air-dried for 20 minutes, oven-dried at 100° C. for 1 hour, and stored in a desiccator.

B. Fluorinated Celite

Fluorinated Celite surfaces comprising rehydrated Celite reacted with 0.3 equivalent to an excess of fluoride to $SiO_2$ were prepared by using the following ratios of TBAF and Celite ($SiO_2$):

|  | TBAF | | | Celite* | |
|---|---|---|---|---|---|
| Rxn | eq. | ml | mMol | g | mMol |
| 1 | 0.3 | 2.8 | 2.8 | .5 | 8.33 |
| 2 | 0.6 | 5.6 | 5.6 | .5 | 8.33 |
| 3 | 0.9 | 9.0 | 9.0 | .5 | 8.33 |
| 4 | exs | 12.0 | 12.0 | .5 | 8.33 |

*Celite 545 was oxidized prior to use by acid washing with $HNO_3$ or $H_2SO_4$.

Reaction 1 was performed as described for reaction 1 of the fluorinated Al(OH)₃ surfaces. Reactions 2–4 were performed as described for reactions 2 and 3 of the fluorinated Al(OH)₃ surfaces.

EXAMPLE 2

Analysis of DNA Recovery Using Super Fine Super Floss Celite as Standard

The following materials were utilized for the analysis of DNA recovery with super fine super floss Celite as a standard for the analysis of the DNA recovery capabilities of the silicon-containing materials:

Super Fine Super Floss Celite (Manville; 1:5 w/w in $H_2O$) [SFSF]
μDNA (BRL Cat. No. 56125A)
50 mM Tris, pH 7.0 (diluted from 1M stock)
Binding buffers ($H_2O$ or $NaClO_4$ diluted from 6M stock)
80% ethanol in 50 mM Tris, pH 7.0
MilliQ $H_2O$
Ethidium bromide (10 mg/ml)
1% agarose
1X TAE (diluted from 50X stock)
Type II loading dye (25% Ficoll 400, 25% bromophenol blue, 25% xylene cyanol)
Types 57 and 55 Polaroid film Fifty μl of λ DNA solution (0.5 μl λ DNA in 50 μl 50 mM Tris, pH 7.0, for 31 μg DNA/reaction) were added to eight tubes. Twenty μl of SFSF was added to the DNA (~30 μg). Four hundred μl of binding buffer was added to the DNA as follows: $H_2O$ to tube 1; 1.0, 1.5, 2, 2.5, 3, 3.5 and 4M $NaClO_4$ to tubes 2–8, respectively. The mixture was incubated with rocking for 10 minutes at room temperature. The tubes were centrifuged and the supernatant was discarded. Resulting pellets were washed twice with 80/20 ethanol/50 mM Tris HCl, pH 7.0. The DNA was eluted from the pellet in 20 μl water for 10 minutes at 37° C. The tubes were centrifuged and the supernatants of each saved in a separate tube. The pellets were eluted again, as before, the tubes centrifuged and the supernatants combined. Two μl of Type II loading dye was added to each tube of the supernatants and the mixture loaded into a 1% agarose, 1X TAE gel. The gel was run for about 25 minutes at 100–130 volts in 1X TAE buffer. The gels were stained with ethidium bromide in $H_2O$ (~1:1000) for ~20–30 minutes. Photographs over UV light were taken with Type 57 film and negatives were taken (when possible) with Type 55 film.

The gels showed that a small amount of DNA eluted from the SFSF with water used as the binding buffer. A small amount of DNA was also eluted with 1, 1.5 and 2.0M $NaClO_4$ used as the binding buffer. A dramatic rise in the amount of eluted DNA was seen with 2.5, 3.0, 3.5 and 4.0M $NaClO_4$ used as the binding buffer. When SFSF was compared with Prep-A-Gene™, it was seen that no DNA was eluted from the Celite from Prep-A-Gene™ until 3.0M $NaClO_4$ was used as the binding buffer, whereas SFSF bound some DNA in its native state and bound it more strongly at 2.5M $NaClO_4$. Thus, SFSF performed better than Prep-A-Gene™. In the Examples which follow, SFSF was used as the standard, using 3M $NaClO_4$ as the binding buffer.

EXAMPLE 3

Analysis of DNA Recovery Using Fluorinated Al(OH)₃

The recovery of DNA using the fluorinated Al(OH)₃ prepared in Example 1 was analyzed by following the procedure set forth in Example 2, except that seven tubes contained the fluorinated Al(OH)₃ 20 μl suspension (~30 μg) and 1, 1.5, 2, 2.5, 3, 3.5 and 4M $NaClO_4$ (400 μl each) was used as the binding buffer. The eighth tube (control) contained SFSF 20 μl suspension (~30 μg) and used 3.0M $NaClO_4$ as the binding buffer. The following results were obtained. A fluorinated Al(OH)₃ reacted with 0.3 equivalent of fluorine to Al(OH)₃ (reaction 1) showed good recovery (i.e., binding and eluting) of DNA down to 1.5M $NaClO_4$ (i.e., 1.5M $NaClO_4$ used as the binding buffer), out-performing SFSF. A fluorinated Al(OH)₃ reacted with 0.3 equivalent of fluorine gave excellent recovery of DNA, out-performing Prep-A-Gene™ (see Example 5).

EXAMPLE 4

Analysis of DNA Recovery Using Fluorinated Celite

The recovery of DNA using fluorinated Celite prepared in Example 1 was analyzed as described in Example 3. The following results were obtained. A fluorinated Celite prepared by reacting 0.3 equivalent of fluorine to rehydrated Celite, prepared by reaction 1 but without refluxing, did not recover any DNA. A fluorinated Celite reacted with 0.3 equivalent of fluorine prepared by reaction 1, eluted some DNA down to 2M $NaClO_4$. A fluorinated Celite prepared by reacting 0.6 or 0.9 equivalent of fluorine, prepared by reaction 2 or 3, eluted DNA down to 1M NaClO$_4$ with good amounts eluted down to 1.5M NaClO$_4$. A fluorinated Celite prepared by reacting excess fluorine prepared by reaction 4, gave DNA recovery down to 1.5M NaClO$_4$.

EXAMPLE 5

Analysis of Quantitative DNA Recovery

A 1:10 dilution of λ DNA (500 µg DNA in 658 µl TE buffer (10 mM Tris-HCl, 1 mM EDTA, pH 8.0)) was prepared. DNA samples were prepared, each containing 10 µl of the diluted λ DNA and 230 µl TE buffer. A standard DNA sample was prepared containing 40 µl TE buffer and 10 µl of the diluted λ DNA. Thirty µl of Al(OH)$_3$, fluorinated Al(OH)$_3$ (reaction 3 of Example 1) and Prep-A-Gene™ Celite were added to the DNA samples, followed by 750 µl of Prep-A-Gene™ binding buffer. The samples were shaken for 10 minutes at room temperature. The samples were centrifuged and decanted. The binding step, including centrifugation and decanting, was repeated. Five hundred µl Prep-A-Gene™ wash buffer was added, and the samples were shaken for five minutes at room temperature. The samples were centrifuged, decanted and dried at 60° C. for 10 minutes. Twenty-five µl of Prep-A-Gene™ elution buffer was added, the sample mixed and then heated at 60° C. for 10 minutes. The samples were centrifuged and the supernatants combined. Gel electrophoresis was performed as described in Example 2, with 3 µl of Type II loading dye added to 7 µl eluted DNA. Gel electrophoresis showed that no DNA was eluted from the Al(OH)$_3$ surface, whereas DNA was eluted from the fluorinated Al(OH)$_3$ and Prep-A-Gene™ Celite.

The samples were also analyzed by a tri-carb 300 scintillation counter. Three samples from each of the different surfaces were counted to determine the location of the DNA. These samples were: (1) the original binding buffer following the first binding step; (2) the elution buffer after the second elution step, and (3) the binding matrix (surface). The analysis was conducted as follows: (1) two volumes of 6 ml scintillation fluid were added to the binding buffer; (2) 6 ml scintillation fluid was added to 40 µl of the elution buffer, and (3) 6 ml scintillation fluid was added to the binding matrix. This analysis showed that Al(OH)$_3$ removed more DNA (94.9%) from the original solution than the other two surfaces. However, 99.3% of what was bound remained bound to the surface following elution. The fluorinated Al(OH)$_3$ bound 24.2% of the DNA, more than the Prep-A-Gene™ Celite. 74.6% of the bound DNA eluted from the fluorinated Al(OH)$_3$. This amount of DNA was greater percentage-wise than with the Prep-A-Gene™ Celite.

Fluorinated Celite was also analyzed with the gel electrophoresis technique. DNA was recovered from the fluorinated Celite prepared by reaction 1 of Example 2.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

What is claimed is:

1. A method for purifying DNA comprising the steps of:

(a) contacting a suspension containing DNA with a fluorinated surface prepared by reacting rehydrated Celite with from about 0.05 equivalent to an excess of fluoride ion under conditions suitable to bind DNA to said surface;

(b) washing said fluorinated surface having bound DNA; and (c) eluting the DNA from said fluorinated surface.

2. A method for purifying DNA comprising the steps of:

(a) contacting a suspension containing DNA with a fluorinated surface prepared by reacting rehydrated Celite with from about 0.3 to about 0.9 equivalent of fluoride ion under conditions suitable to bind DNA to said surface;

(b) washing said fluorinated surface having bound DNA; and (c) eluting the DNA from said fluorinated surface.

* * * * *